United States Patent [19]
Burns

[11] Patent Number: 5,891,103
[45] Date of Patent: *Apr. 6, 1999

[54] SHIELDED NEEDLE ASSEMBLY

[75] Inventor: James A. Burns, Elizabeth, N.J.

[73] Assignee: Becton Dickinson and Company, Franklin Lakes, N.J.

[ * ] Notice: The term of this patent shall not extend beyond the expiration date of Pat. No. 5,643,219.

[21] Appl. No.: 808,929

[22] Filed: Feb. 28, 1997

Related U.S. Application Data

[63] Continuation of Ser. No. 310,538, Sep. 23, 1994, Pat. No. 5,643,219.

[51] Int. Cl.$^6$ ................................................. A61M 5/32
[52] U.S. Cl. .................................... 604/192; 604/263
[58] Field of Search .................................. 604/198, 263, 604/192, 187, 110; 128/919; 206/364, 365, 570, 571

[56] References Cited

U.S. PATENT DOCUMENTS

| | | | |
|---|---|---|---|
| 4,834,715 | 5/1989 | Hanifl | 604/192 |
| 5,055,102 | 10/1991 | Sitnik | 604/192 |
| 5,439,453 | 8/1995 | Kashanchi | 604/263 |
| 5,445,619 | 8/1995 | Burns | 604/192 |
| 5,490,841 | 2/1996 | Landis | 604/192 X |

Primary Examiner—Ronald Stright, Jr.
Assistant Examiner—A. T. Nguyen
Attorney, Agent, or Firm—Nanette S. Thomas; Arthur D. Dawson

[57] ABSTRACT

A safety needle assembly includes a needle having a longitudinal axis, a length, a pointed distal end, a proximal end and a passageway therethrough. The assembly includes a hub having a longitudinal axis, a proximal end, a distal end and an outside surface with an outside diameter. The hub has an axial opening through it for receiving the needle so that the distal end of the needle projects outwardly. The hub has a circumferential groove in the outside surface and a raised annulus located proximally to the groove. The assembly includes a shield with an open end, a closed end, a sidewall with a longitudinal slot extending from the open end toward the closed end. The shield has a first position exposing the needle and a second position wherein the shield obstructs unintentional access to the needle. The shield has a mounting for holding the shield onto the hub with a first portion having an opening for placement on the hub at the groove. The opening has at least one inward projection sized to fit within the groove and rotatably hold the mounting on the hub. The mounting attaches to the shield with a hinge opposite the slot, so that when the slot is moved from the first position to the second position, the slot provides clearance for the needle. The shield further includes at least one lug to engage the annulus and lock the shield in the second position

13 Claims, 8 Drawing Sheets

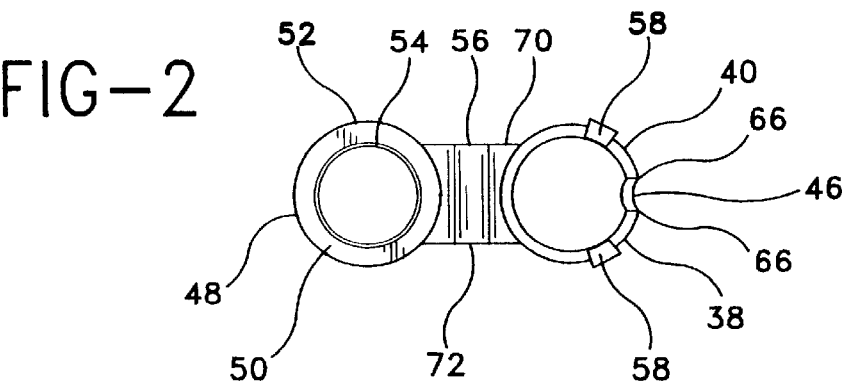
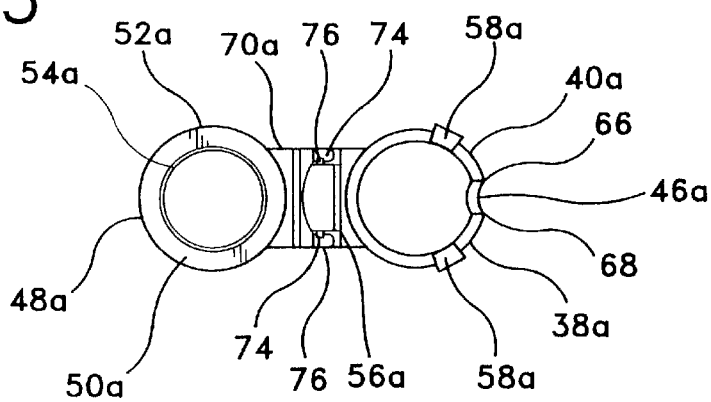
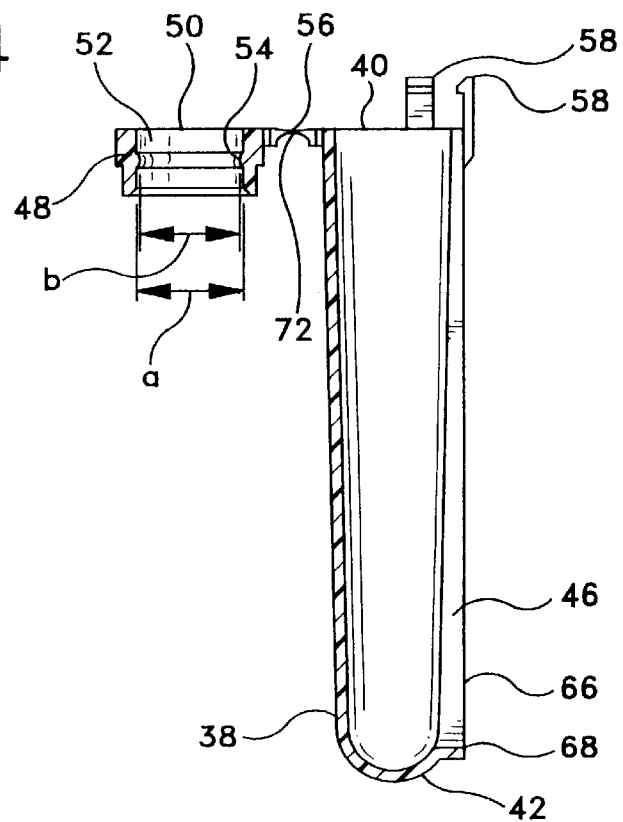

SHIELDED NEEDLE ASSEMBLY

This is a continuation of application Ser. No. 08/310,538, filed Sep. 23, 1994, now U.S. Pat. No. 5,643,219.

BACKGROUND OF THE INVENTION

1. Field of Invention

The present invention relates to a safety shield for a needle and more particularly to a shield assembly which attaches to the hub of the needle, and allows use of the needle on a syringe, needle holder or other fluid handling device.

2. Description of Related Information

In the medical arts, sharp pointed needles are used for a variety of procedures. Devices having sharp pointed needles are used for administering fluids to patients either directly or into intravenous apparatus, and in various blood drawing applications either with syringes or with specialized holders for filling evacuated tubes.

Exposure to blood borne pathogens is a recognized hazard by anyone associated with the medical arts. As a result of this recognition, numerous protocols for use of needles have been developed and are practiced. The problem of transmission of blood borne pathogens not only exists for the physician, nurse or phlebotomist using the needles, but also for support workers all through the hospital. Since most needles in use today are single-use and disposable, hospital service personnel are at risk from needles that are not properly handled by the users.

The use protocols generally dictate in detail when and how a needle will be used and how it should be disposed of. The problem with many protocols for handling needles is that the protocols often require users to perform additional steps in a procedure. With the press of time and simple carelessness certain practices regarding handling of used needles are sometimes disregarded and injuries still occur. The medical device industry has responded to the problem by producing a wide variety of sharps collectors, needle shielding devices and the like to assist practitioners in their need to reduce the occurrence of needle injuries.

Many devices have been developed for shielding needles after use to avoid exposing other workers to used needles. A representative listing of many of these devices is found in U.S. Pat. No. 4,982,842 to Hollister et al. Hollister et al. lists 90 U.S. patents of various devices for guarding a needle as part of the background for the present shielded needle container. Hollister et al. discloses a stand alone adapter that has a male and female end for mating with a needle assembly and the ejection end of a syringe. The device of Hollister et al. includes a housing mounted to the adapter which may be pivoted to a position in alignment with the needle for enveloping the needle and locking the needle to retain it in the housing. The Hollister et al. device increases the unusable or "dead" volume of the device on which the adapter is mounted, requires an additional part which increases the projection of the needle hub, and the mechanism for holding the cap onto the needle snaps onto the needle itself, which may create an aerosol of any fluid remaining on the needle. Also, if bevel position is important to the intended use of the needle, the Hollister et al. invention must be carefully aligned with the needle point when mounted.

U.S. Pat. No. 5,207,653 to Janjua et al. discloses a needle cap with a longitudinal slit having a width greater than the width of a needle. According to Janjua et al., the needle cap is adapted to be pivotally connected with the needle and hub piece. Janjua et al. also discloses that the needle cap is usable with a syringe or with a needle holder for fluid collection tubes. The device disclosed by Janjua et al. mounts on the needle hub with a pivot, but since it only pivots in one plane, unless the needle point is precisely with the hub oriented during assembly, the shield may interfere in some applications.

Many of the devices listed in the background of the Hollister et al. patent, the Hollister et al. invention itself and the Janjua et al. invention all attempt to address the recognized need to protect medical and service personnel from needle sticks. There are several recurrent problems in varying degrees with all these devices. Many of the devices are somewhat complex, hence are significantly more costly than an unprotected device. Many of the devices increase the complexity or increase the difficulty of performing a procedure. Some devices are so specific that they preclude use of the device in certain procedures. For these and similar reasons most of the devices in the Hollister et al. background have never been successfully commercialized.

Blood drawing is one application that is particularly sensitive to needle point orientation. Most phlebotomists carefully align a needle point with the beveled face away from the skin so that the needle point placement may be precisely controlled. A needle assembly as disclosed in Janjua et al. would either sometimes be clumsy to use because the shield would sometimes be in the way or, alternatively, more expensive because of the need to carefully orient the point during manufacture. Additionally, in Janjua et al., while there is a recognition of the need to secure the cap in the closed position over the needle, all of the solutions proposed require additional steps such as securing the cap with an adhesive or twisting the cap.

Although there already are many shielded needle devices, there is still a need for a shielded needle device that is easily manufactured, applicable to many devices and simple to use. Additionally, the needle device should not interfere with normal practices of use. Such a device is described below.

SUMMARY OF THE INVENTION

A shielded needle assembly includes an elongate needle with a passageway therethrough. The needle has a proximal end and a pointed distal end. The assembly preferably includes a hub having a proximal end, a distal end and an outside surface. Preferably the hub has an[ ]axial opening therethrough for receiving the needle so that the distal end of the needle projects outwardly. Preferably, the hub further includes elements for releasably mounting the hub on a fluid handling device. The preferred assembly includes a shield with an open end, a closed end and a sidewall with a slot extending from the open end toward the closed end. The shield has a first position where the needle is exposed for use and a second position where the shield substantially obstructs access to the needle. The preferred shield has a rotatable mounting for holding the shield onto the hub. Preferably, the first portion has a hinge attached to the open end of the shield opposite to the slot. The slot preferably is sufficient to provide a clearance for the needle thereby allowing the shield to pivot on the hinge from the first position to the second position. The open end of the shield preferably has at least one element to lock the shield in the second position.

In the preferred embodiment the needle projects proximally outwardly from the hub and includes a proximal point for penetrating a stopper of a fluid collection tube. In this embodiment, the elements for releasably mounting the hub preferably include a proximal thread for mounting the hub on a tube holder.

In another embodiment, the elements for releasably mounting the hub on a fluid handling device preferably include a proximal female luer fitting which may be mounted on a syringe or other fluid handling device having a male luer fitting.

The needle assembly of the present invention is simple to manufacture and since it is rotatably mounted on the hub, no requirement to orient the point is imposed on the manufacturing process. The needle shield can be easily rotated out of the way when the needle is in use, and is easily moved to the closed position substantially preventing inadvertent access to the needle. The needle shield locks in the closed position without requiring any additional action by the user.

BRIEF DESCRIPTION OF THE DRAWINGS

FIG. 2 is a sectional view along the line 2,2 of the shield and mounting portion of the embodiment of FIG. 1;

FIG. 3 is a sectional view, similar to the view of FIG. 2, illustrating an alternate embodiment of the hinge;

FIG. 4 is a cross sectional view of the shield and mounting portion of the embodiment of FIG. 1 along the line 4,4;

DETAILED DESCRIPTION OF THE INVENTION

Figure 1:
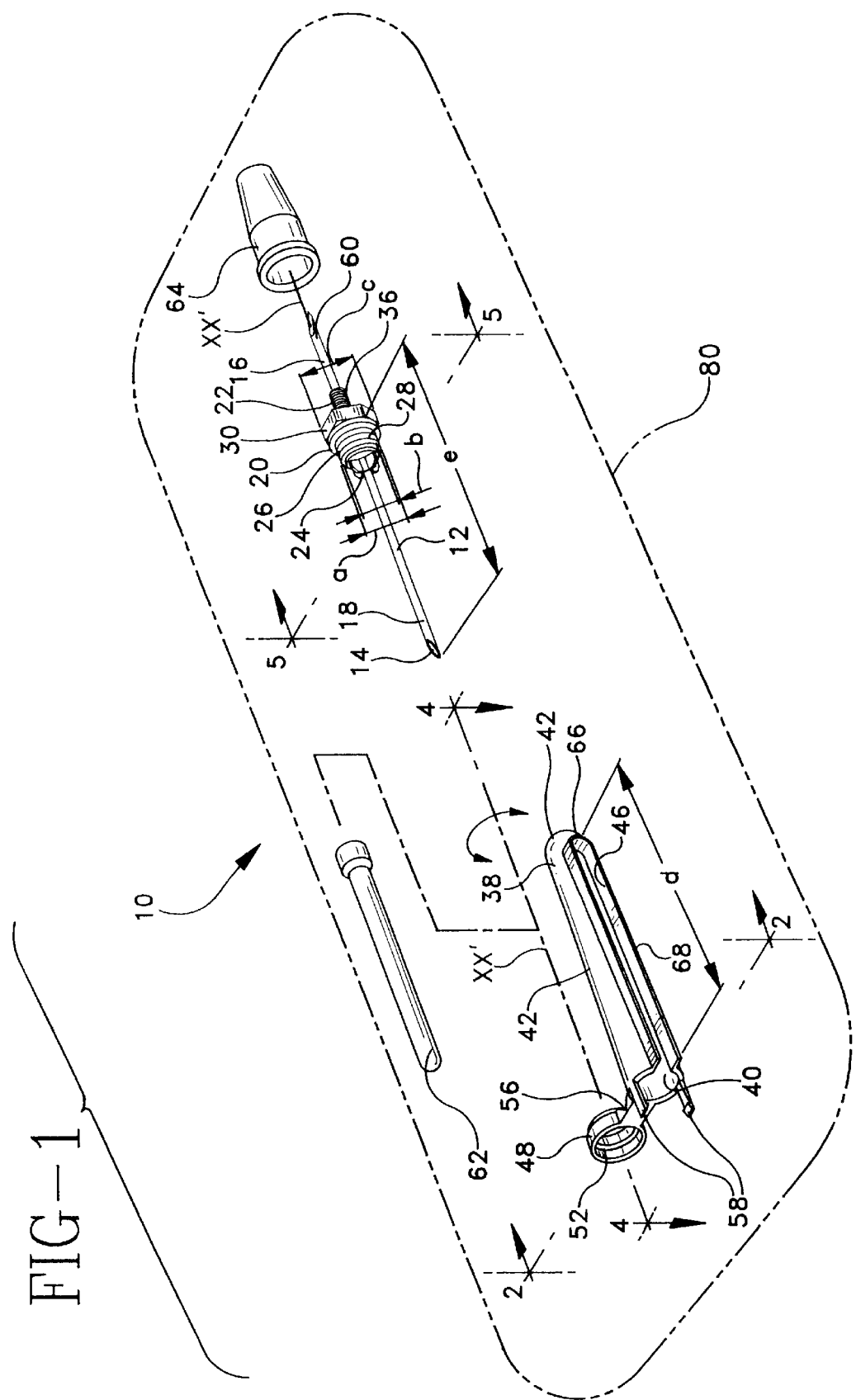
FIG. 1 is an exploded perspective view of a preferred embodiment of the present invention.
Figure 5:
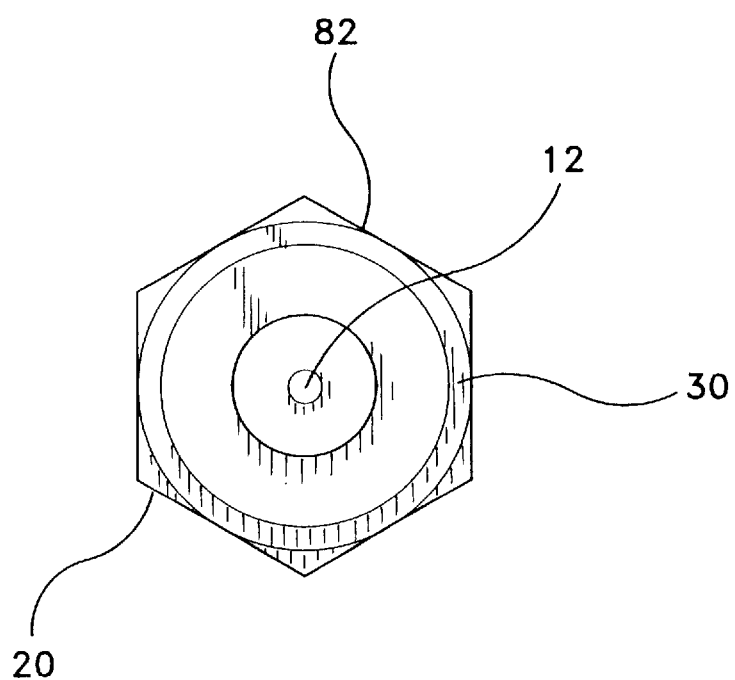
FIG. 5 is a sectional view along the line 5,5 of the hub portion of the embodiment of FIG. 1.

While this invention is satisfied by embodiments in many different forms, there is shown in the drawings and will herein be described in detail, several embodiments of the invention with the understanding that the present disclosure is to be considered as exemplary of the principles of the present invention and is not intended to limit the scope of the invention to the embodiments illustrated. The scope of the invention will 6e measured by the appended claims and their equivalents.

A convention adopted for this disclosure is that the term "distal" refers to the direction away from a user of the invention and the term "proximal" refers to the direction toward the user.

Referring to FIGS. 1 to 7, a shielded needle assembly 10 of the present invention includes a needle 12 having a longitudinal axis X, a pointed distal end 14, a proximal end 16 and a passageway 18 therethrough. The preferred assembly includes a hub 20 having a longitudinal axis X', a proximal end 22, a distal end 23 and an outside surface 26 having an outside diameter a. Hub 20 preferably has an opening 24 for receiving needle 12 so that distal end 14 projects outwardly. Hub 20 preferably has a circumferential groove 28 in outside surface 26 with an outside diameter b which is less than hub outside surface diameter a. Hub 20 preferably also includes a raised annulus 30 with an outside diameter c which is greater than hub outside surface diameter a. Preferably, hub 20 includes elements 32 for releasably mounting the hub on a fluid handling device. In the preferred embodiment where the fluid handling device is a needle tube holder 34, elements 32 are preferably male threads 36 on proximal end 22 for mounting the hub on tube holder 34.

Figure 6:
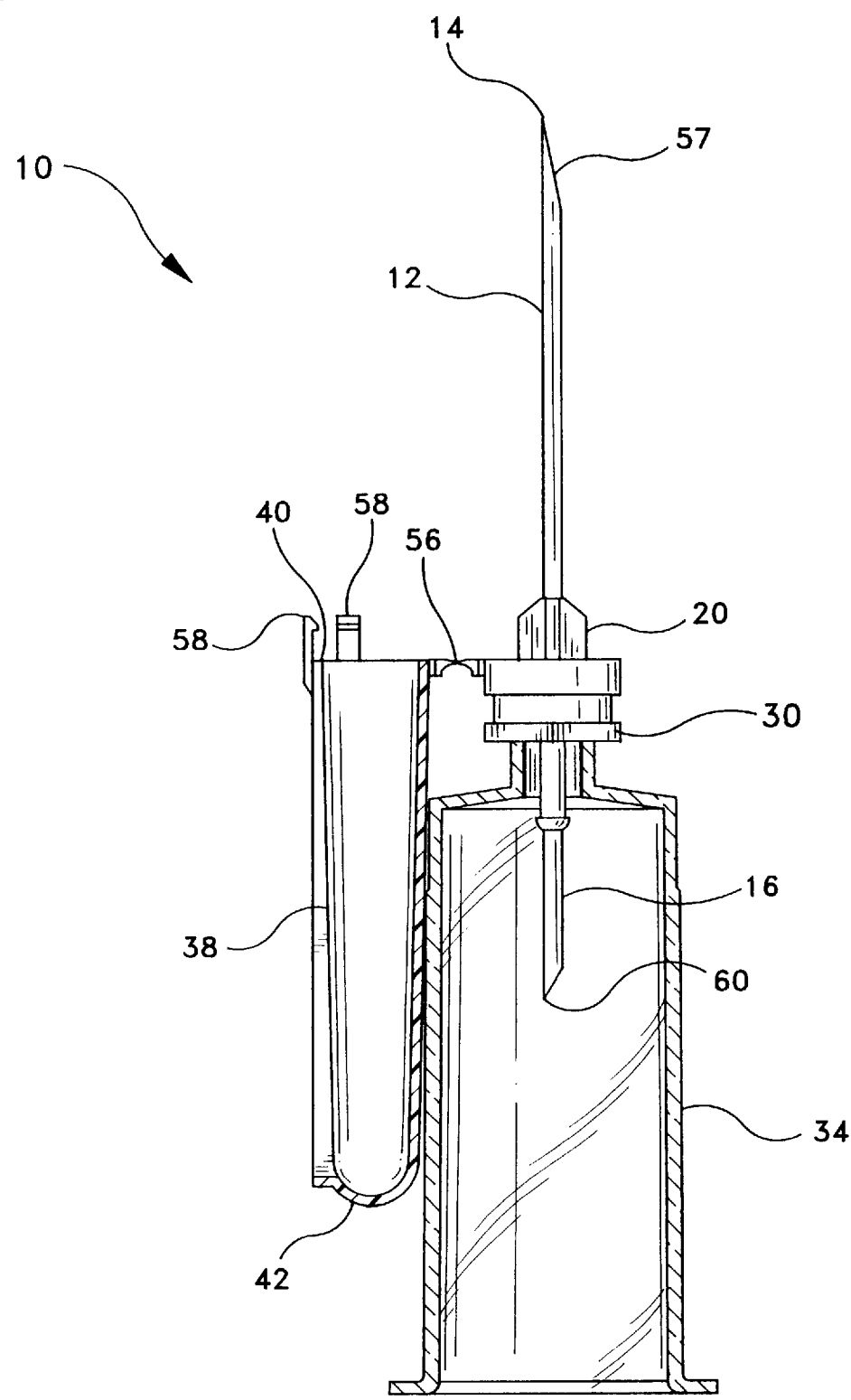
FIG. 6 is a schematic cross sectional view of the embodiment of FIG. 1 mounted on a needle holder with the shield in the first position.
Figure 7:
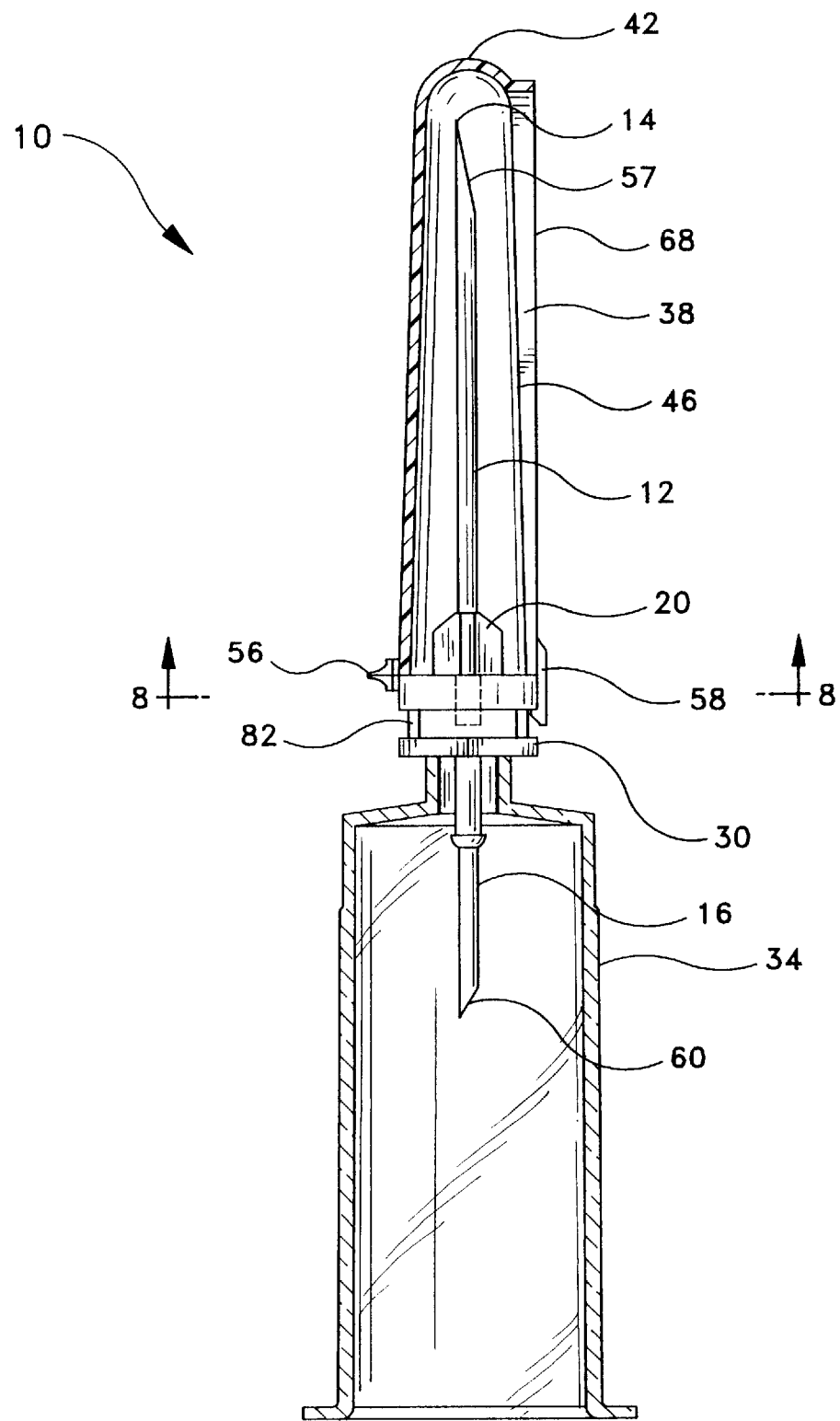
FIG. 7 is a schematic cross sectional view of the embodiment of FIG. 6 with the shield in the second position.

Needle assembly 10 preferably further includes a shield 38 having an open end 40, a closed end 42 and a sidewall 44 having an open slot 46 extending a length d from open end 40 toward closed end 42. As illustrated in FIG. 6, shield 38 has a first position at which needle 12 is exposed for use. FIG. 7 illustrates shield 38 in a second position at which shield 38 substantially obstructs unintentional access to needle 12.

Shield 38 preferably has a mounting 48 for holding shield 38 onto hub 20 including a first portion 50 having an opening 52 therethrough for placement onto the hub at groove 28. Opening 52 preferably includes at least one inward projection 54 sized to fit within groove 28 for holding mounting 48 on hub 20 while allowing free rotation of the mounting about the hub. First portion 50 has a hinge 56 attached to shield 38 at open end 40 diametrically opposite slot 46.

A particular benefit of the rotatable mounting for shield 38 is that the shield may be rotated about hub 20 so that the shield does not interfere with a procedure such as blood drawing. The technique practiced by phlebotomists in venepuncture generally requires that the distal point of the needle be aligned so that a face 57 of the beveled needle point 14 is up (away from the patient). This bevel placement allows the needle point to be precisely positioned for the puncture. In performing the penetration of the vein, the goal is to minimize the angle of entry. A minimum angle of entry reduces the incidence of penetration of the far wall of the vein in the venepuncture. Most other shield devices are attached to the tube holder or to the hub with a fixed pivot and the like, thus requiring careful orientation of the needle point to the hub during the manufacture of the device. The need for point orientation imposes an additional and critical requirement on the device manufacturing process, adding an additional step, potentially slowing the rate of manufacture and possibly decreasing the yield. Since the shield rotates about the hub, the present invention requires no orientation of the needle point during manufacture, retaining the process and equipment currently used for conventional needle assemblies.

The clearance provided by slot 46 allows shield 38 to pivot on hinge 56 from the first position to the second position where the shield obstructs access to the needle. Shield open end 40 further includes at least one lug 58 for engaging annulus 30 when shield 38 is in the second position.

In the preferred embodiment where assembly 10 is intended for use in a needle holder, proximal end 16 of the needle preferably projects outwardly from hub 20 and includes a proximal point 60 for penetrating a stopper of a fluid collection tube. One skilled in the art of medical devices will recognize that needle 12 may be formed as a single article having a proximal point on a proximal portion projecting proximally and a distal point on a distal portion projecting distally. Alternately, needle 12 may be two separate pieces, a distal piece projecting distally having a distal point and a proximal piece projecting proximally having a proximal point, with the pieces connected in fluid communication in the hub opening. Preferably, safety needle assembly 10 includes a removable distal cover 62 releasably mounted on hub 20 for covering needle 12 projecting distally from the hub. Distal cover 62 provides physical protection for distal point 14 and may serve as a barrier to passage of microorganisms until it is removed prior to use. Assembly 10 preferably includes a removable proximal cover 64 mounted on hub 20 for covering proximal needle end 16 projecting from the hub. Proximal cover 64 provides physical protection for proximal point 60 and may provide a barrier to passage of microorganisms until the proximal cover is removed. Assembly 10 preferably is sealed in a package (schematically illustrated as reference number 80 in the drawings) formed from materials resistant to the passage of microorganisms and exposed to conditions that render any microorganisms present in the package substantially nonviable. Generally, in the medical device industry, exposure of a packaged device to ethylene oxide or to gamma radiation is used to render microorganisms nonviable and the device within the package is defined as sterile. A packaged safety needle assembly would be sterile until package 80 was opened for use. Additionally, covers 62 and 64 serve to keep needle 12 sterile until they are removed for immediate use.

Slot 46 in the sidewall of shield 38 has a perimeter 66 which preferably includes a raised rib 68. Raised rib 68 serves to stiffen shield 38 and to substantially reduce incidence of spatter from any residual fluid on needle 12 when the shield is in the second position.

It is preferred that shield 38 and mounting 48 with first portion 50 and hinge 56 be formed as a unitary article of manufacture. Hinge 56 preferably is formed as a "living hinge" when the shield and mounting are formed. Preferably shield 38 and mounting 48 are formed by injection molding a thermoplastic resin. It is well known in an injection molded article, if an area of the article has a reduced thickness relative to its surrounding area and the molded part is flexed at the area of reduced thickness immediately after the part is removed from the injection molding tool, the area of reduced thickness functions as a hinge because the polymer molecules of the resin are oriented by the flexion. If the article is not flexed immediately, the ability to form a hinge is lost, hence the term "living hinge." In the preferred shield and mounting, hinge 56 includes a strip 70 with an area of reduced thickness 72 which is preferably formed into a living hinge when the article is freshly removed from the mold tool.

FIG. 3 shows an alternate embodiment to the hinge similar to the cross-sectional view illustrated in FIG. 2. In this embodiment, there are elements similar in structure and function to the embodiment of the present invention shown in FIG. 1. Accordingly, substantially similar components that perform substantially similar functions are numbered identically to those components of the embodiment of FIG. 1 except that a suffix is added to identify those components in FIG. 3. As shown in FIG. 3, shield 38a and mounting 48a may be individually formed and joined by hinge 56a which includes rotatable mechanical elements such as pins 74 mounted in recesses 76. The actual form of the mechanical hinge is not critical to the invention. Other types of rotatable mechanical hinges are also satisfactory.

Shield 38 and mounting 48 may be formed from thermoplastic resins such as polyvinyl chloride, polystyrene, polypropylene, polycarbonate, polyethylene and the like. Polypropylene, polyethylene, and copolymers of polypropylene and polyethylene are preferred, as they are particularly suited for the formation of living hinges.

Shield 38 preferably has two lugs 58 to engage annulus 30 when the shield is in the second position. When lugs 58 engage annulus 30, shield 38 is locked in the second position, substantially preventing inadvertent contact with needle 12.

In normal usage of the preferred needle assembly for drawing a blood sample, proximal cover 64 is removed from the assembly and hub 20 mounted in needle holder 34 using threads 36. Immediately prior to the procedure, distal cover 62 is then removed exposing needle point 14. Face 57 of the beveled needle is aligned to face away from the patient. During the alignment, the practitioner rotates shield 38 around hub 20 so as not to interfere with the placement of the needle point. The precise position allows the practitioner to minimize the angle of entry of the needle into the vein. A minimum penetration angle reduces the incidence of penetration of the needle through the far wall of the vein. Needle point 14 is then inserted into the patient's vein and an evacuated blood collection tube with an elastomeric stopper is mounted in the needle holder so that its stopper is penetrated by proximal needle point 60. When the practitioner has completed the blood drawing, the needle is withdrawn from the patient's vein and shield 38 is moved to the second position, obstructing needle 12. As shield 38 is moved to the second position, slot 46 provides clearance for the shield to pass over the needle. Lugs 58 engage annulus 30 when the shield is in the second position and lock shield 38 in the second position.

Figure 8:
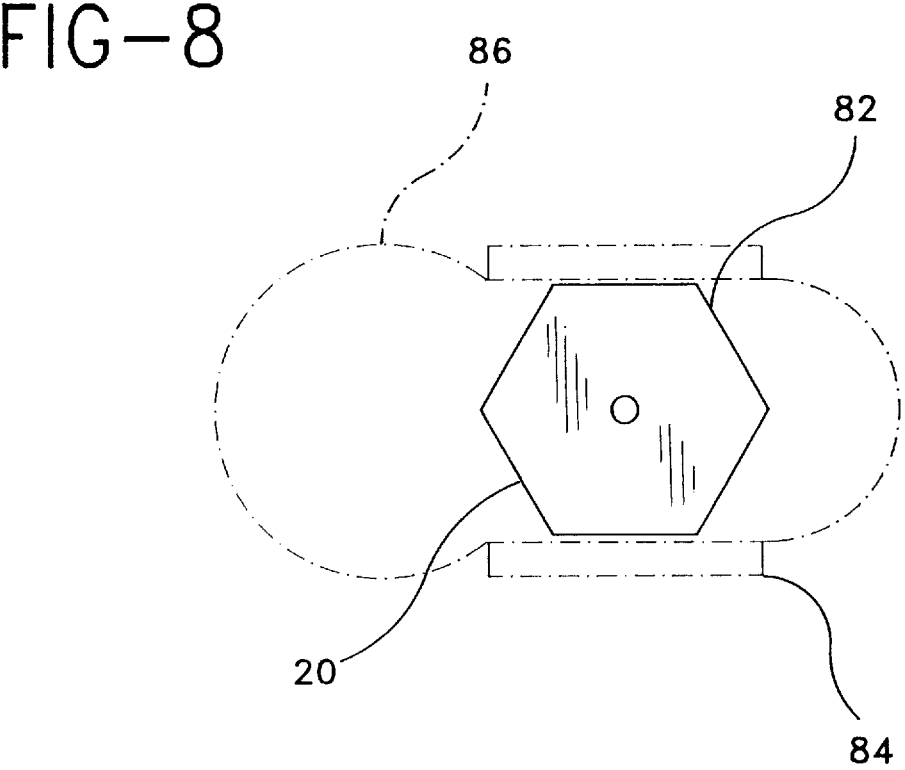
FIG. 8 is a partial schematic cross sectional view along the line 8,8 of the embodiment of FIG. 7 mounted in a needle removal device.
Figure 9:
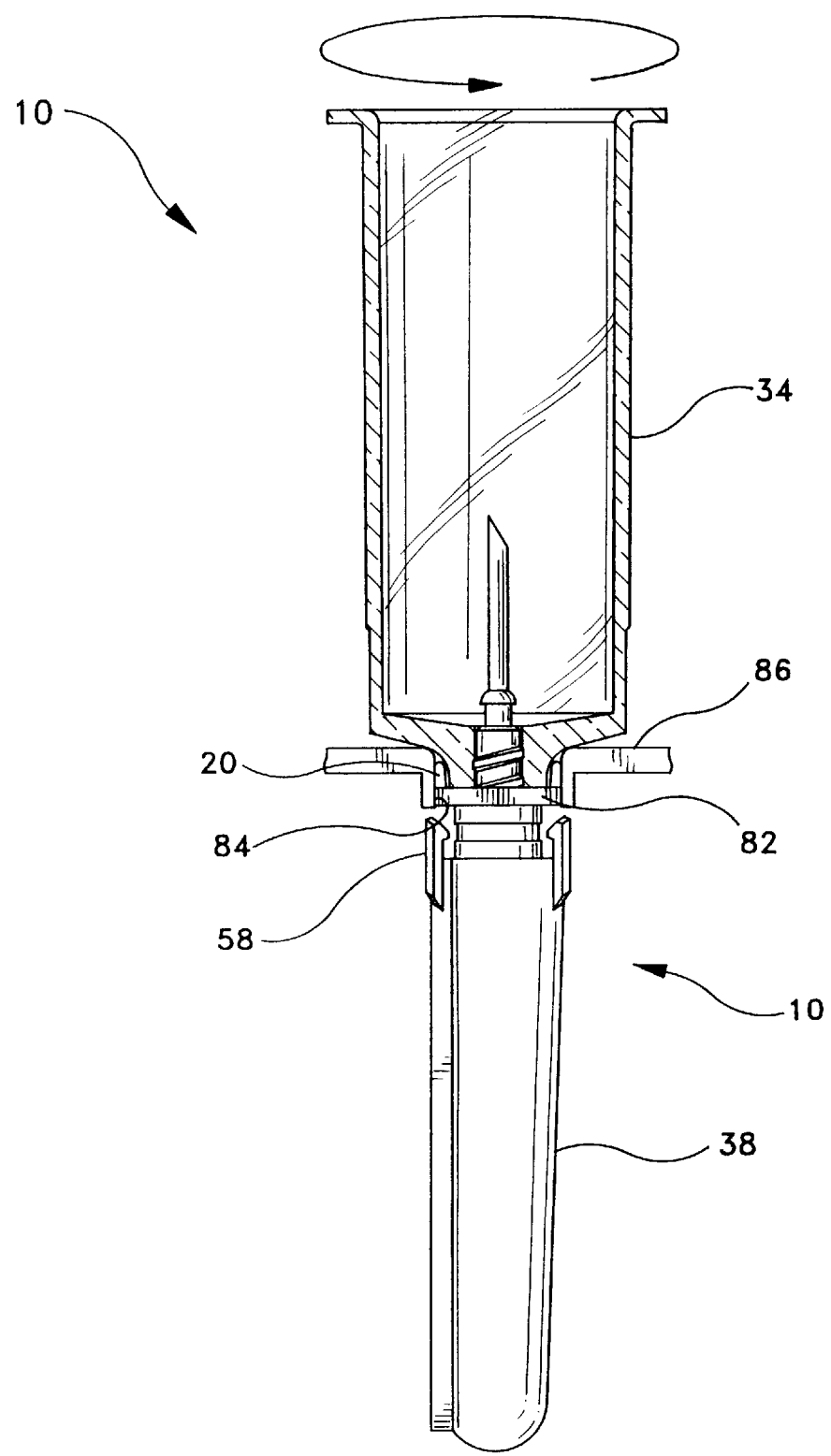
FIG. 9 is a schematic cross sectional view of the embodiment of FIG. 7 mounted in the needle removal device.
Figure 10:
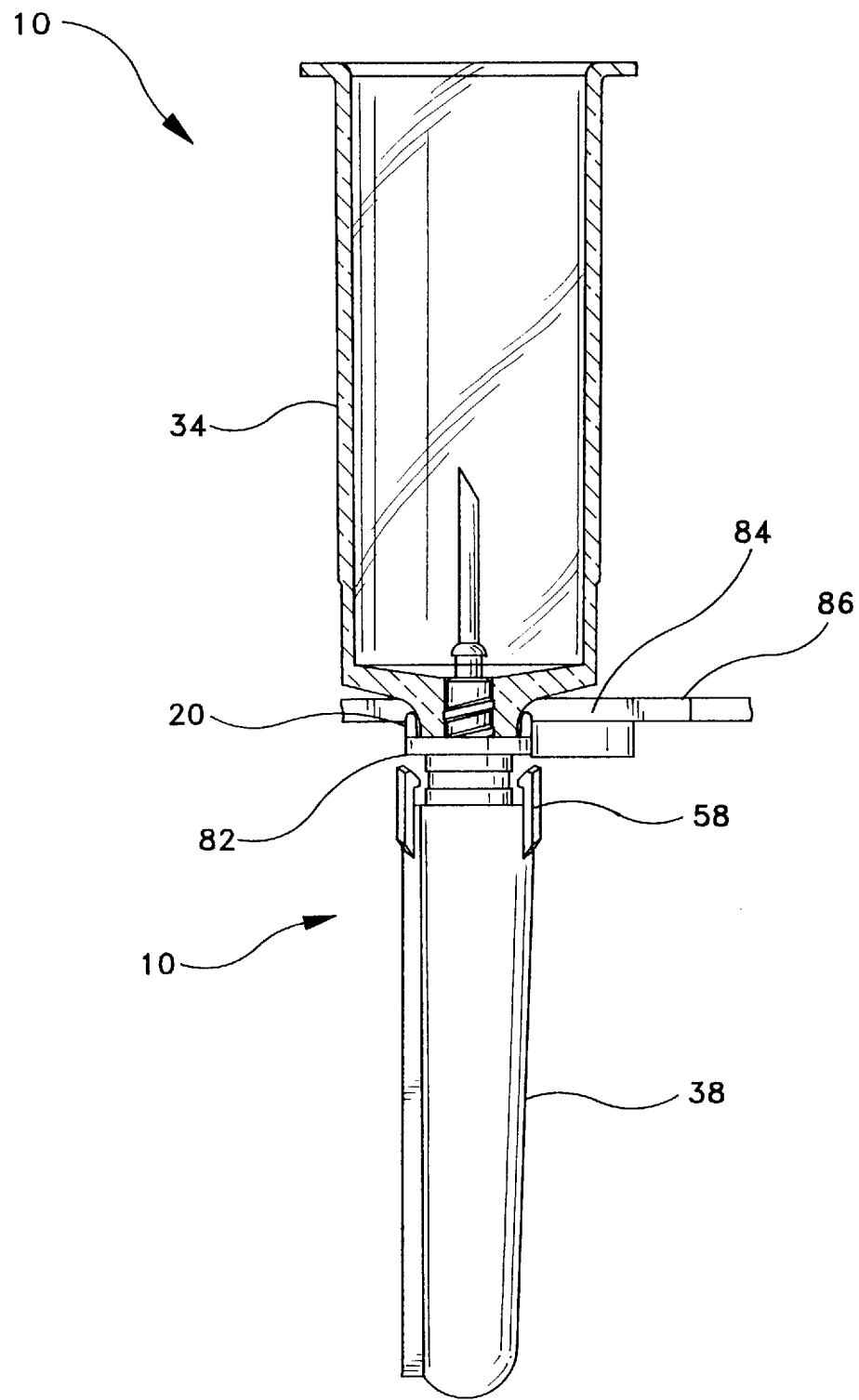
FIG. 10 is a cross sectional view of the embodiment of FIG. 9 mounted in needle removal device.

Referring to FIGS. 8, 9 and 10, hub 20 preferably has a proximal faceted area 82. Preferably faceted area 82 is a hexagon. Faceted area 82 is designed to engage a wrench opening 84 of a safety needle container 86 after the blood drawing procedure is completed and shield 38 is in the second position. The practitioner holds the needle holder and places the needle assembly with shield in the second position into the safety needle container so that faceted area 82 engages the wrench opening of the safety needle container. Needle holder 34 can be easily unscrewed and the needle assembly allowed to fall into the collector for safe disposal. Use of needle assembly 10 imposes little additional requirement on the practitioner. Except for moving shield 38 from the first position to the second position, all the other steps of the blood draw procedure follow normal accepted practice, and needle holder 34 is the standard currently available commercial product.

Figure 11:
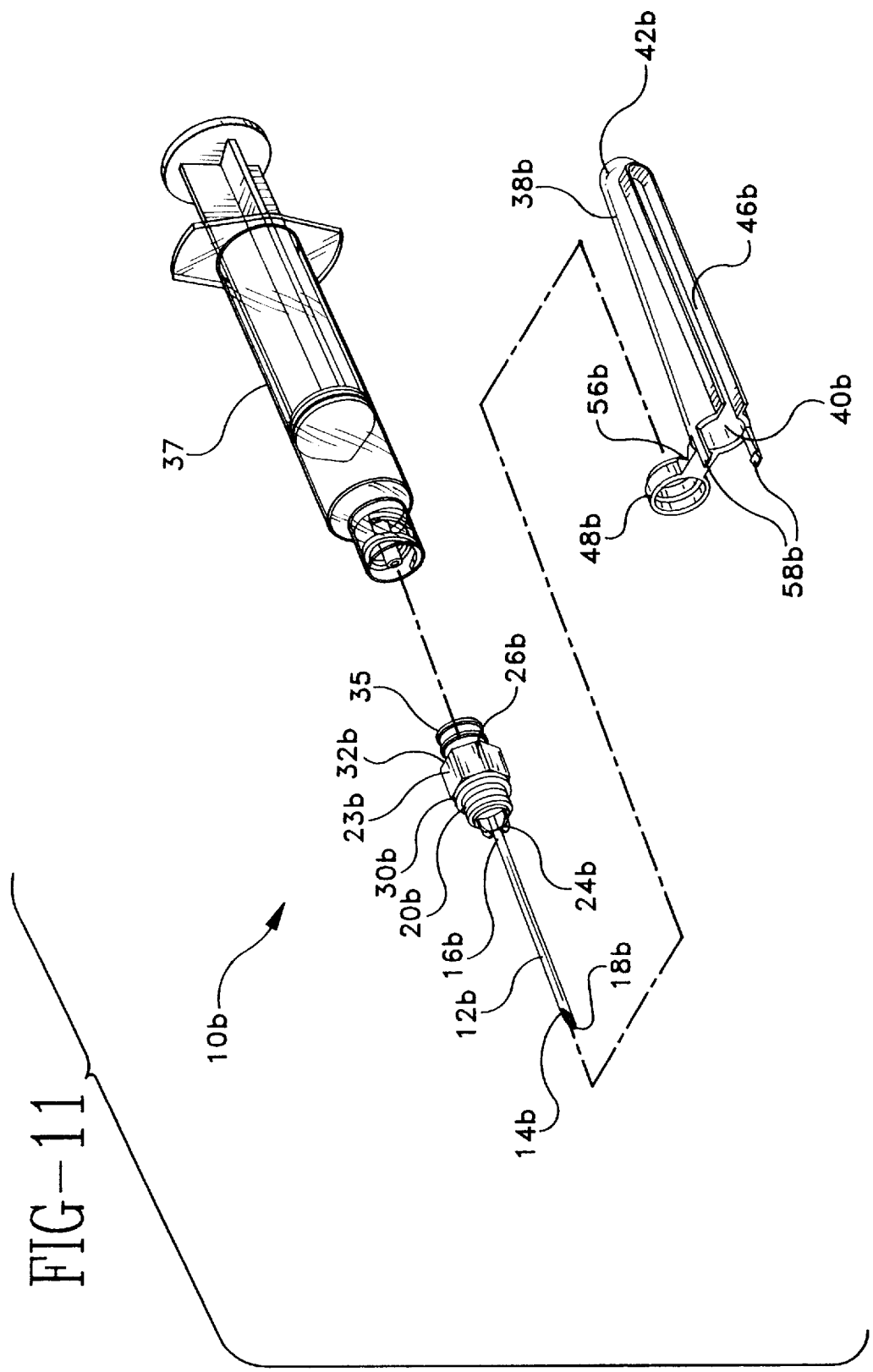
FIG. 11 is an exploded perspective view of an embodiment of the present invention mounted on a syringe with the shield between the first position and the second position.

FIG. 11 shows an alternate embodiment to the shielded needle assembly of FIGS. 1 to 10. In this embodiment, there are elements similar in structure and function to the embodiment of the present invention shown in FIGS. 1 to 7. Accordingly, substantially similar components that perform substantially similar functions are numbered identically to those components of the embodiment of FIGS. 1 through 7 except that a suffix will be added to identify those components in FIG. 8.

As shown in FIG. 11 needle assembly 10b includes a needle 12b having a longitudinal axis Y, a pointed distal end 14b, a proximal end 16b and a passageway 18b therethrough. In this embodiment, elements 32b preferably include a female luer fitting 35 for mounting the hub on a syringe 37 or other fluid handling device such as a catheter.

What is claimed is:

1. A needle assembly comprising:

a elongate needle having a pointed distal end, a proximal end and a passageway therethrough;

a hub having a proximal end, a distal end, and an outside surface, said hub having an axial opening therethrough for receiving said needle so that said distal end of said needle projects outwardly therefrom, said hub further including means for releasably mounting said hub on a fluid handling device;

a shield having an open end, a closed end, a sidewall having a slot from said open end toward said closed end, said shield having a first position wherein said needle is exposed for use and a second position wherein said shield substantially obstructs access to said needle; and said shield having a rotatable mounting for holding said shield onto said hub including a hinge attached to said open end of said shield opposite said slot, said slot being sufficient to provide clearance for said needle thereby allowing said shield to pivot on said hinge from said first position at which said needle is exposed to said second position at which said shield obstructs access to said needle, said open end of said shield further including means for engaging said hub when said shield is in said second position so that said shield is locked in said second position.

2. The assembly of claim 1 wherein said hub outside surface has an outside diameter and includes a circumferential groove having an outside diameter less than said hub outside surface diameter, said hub further including a raised annulus having an outside diameter greater than said hub outside surface diameter located proximally to said groove.

3. The assembly of claim 2 wherein said mounting includes a first portion having an opening therethrough for placement on said hub at said groove, said opening including at least one inward projection sized to fit within said groove on said hub thereby rotatably holding said mounting about said hub.

4. The assembly of claim 1 wherein said means for releasably said hub on said fluid handling device comprise a proximal female luer fitting.

5. The assembly of claim 1 wherein said proximal end of said needle projects proximally outwardly from said hub, said proximal end including a point for penetrating a stopper of a fluid collection tube, and said means for releasably mounting said hub on said fluid handling device comprise a proximal external thread on said hub for mounting said hub on a tube holder.

6. The assembly of claim 5 wherein further including a removable proximal cover releasably mounted on said hub for covering said needle projecting proximally from said hub, and a removable distal cover releasably mounted on said hub for covering said needle projecting distally from said hub, said proximal cover and said distal cover providing physical protection for said proximal point and said distal point respectively until said covers are removed.

7. The assembly of claim 1 further including a removable distal cover releasably mounted on said hub for covering said needle projecting distally from said hub, said removable distal shield providing physical protection for said distal point of said needle until said distal cover is removed.

8. The assembly of claim 1 wherein said hub outside surface has a faceted proximal portion.

9. The assembly of claim 1 wherein said longitudinal slot in said sidewall of said shield has a perimeter comprising a raised rib.

10. The assembly of claim 1 wherein said shield and said mounting are formed as a unitary article of manufacture, and said hinge comprises a strip having a thickness and an area of reduced thickness comprising a living hinge.

11. The assembly of claim 1 wherein shield and said mounting are individually formed and said hinge comprises rotatable mechanical elements.

12. The assembly of claim 1 wherein said shield and said mounting are formed from a thermoplastic resin selected from the group consisting of polyethylene, polypropylene and copolymers of polypropylene and polyethylene.

13. The assembly of claim 1 wherein said assembly is individually packaged in a package substantially providing a barrier to the passage of microorganisms until opened, said package having said assembly therein being exposed to conditions that render microorganisms in said package substantially nonviable.

* * * * *